United States Patent [19]

Suzuki et al.

[11] Patent Number: 4,526,450
[45] Date of Patent: Jul. 2, 1985

[54] EYE FUNDUS CAMERA

[75] Inventors: Toru Suzuki; Eiichi Sano; Yoshihiko Hanamura, all of Tokyo, Japan

[73] Assignee: Tokyo Kogaku Kikai Kabushiki Kaisha, Tokyo, Japan

[21] Appl. No.: 532,994

[22] Filed: Sep. 16, 1983

[30] Foreign Application Priority Data

Sep. 16, 1982 [JP] Japan .................................. 57-159428

[51] Int. Cl.³ .......................... A61B 3/14; G03B 29/00
[52] U.S. Cl. ........................................ 351/206; 354/62
[58] Field of Search .............. 351/205, 206, 207, 208; 354/62

[56] References Cited

U.S. PATENT DOCUMENTS 4,322,137  3/1982  Nohsa .................................. 351/206

Primary Examiner—Rodney B. Bovernick
Attorney, Agent, or Firm—Fleit, Jacobson, Cohn & Price

[57] ABSTRACT

An eye fundus camera adapted to be mounted with a first (12) and a second (20; 26, 27) apparatus for observing and/or photographing the eye fundus, and including a movable mirror (18) moved between a first position where it admits light from the eye fundus to the first apparatus (12) and a second position where it deflects the light toward the second apparatus (20; 26, 27), whereby various modes of operation can be carried out.

5 Claims, 6 Drawing Figures

EYE FUNDUS CAMERA

FIELD OF THE INVENTION

The present invention relates in general to an eye fundus camera and, in particular, to an eye fundus camera which can be mounted with various apparatus for observing and/or photographing the eye fundus in various ways.

BACKGROUND OF THE INVENTION

An eye fundus camera generally has an observing optical system for illuminating and observing the eye fundus, together with a photographic optical system for photographing the eye fundus. A photograph of the eye fundus is taken after the processes of selecting the portion of the fundus to be photographed and focusing by the use of the observing optical system.

Observation of the eye fundus should sometimes be made from various points of view, or by a number of clinicians other than the photographer. A viewfinder enables individual observation of the eye fundus. However, it is sometimes preferable to have means, such as a display tube, which enables simultaneous observation of the eye fundus by all the clinicians. On the other hand, various photographs, such as color photographs and monochromatic photographs, of the fundus of an eye are sometimes required.

However, prior art eye fundus cameras are generally designed to enable a single way of observation and taking only a little number of kinds of photograph. Prior art eye fundus cameras which enable all of the above mentioned ways of observation and kinds of photograph are too large and too cumbersome to operate.

It is thus an object of the present invention to provide an eye fundus camera which is easy to operate and which includes a first and a second apparatus for observing and/or photographing, and in which by means of selection or changeover switches a desired mode of operation of the camera can be selected out of the following three modes of operation: a first mode of operation in which the first apparatus is used for both observation and photographing; a second mode of operation in which the first apparatus is used for individual observation, while the second for photographing; and third mode of operation in which the first apparatus is used for photographing, while the second for observation either individual or simultaneous.

SUMMARY OF THE INVENTION

In order to achieve the above object, the present invention provides an eye fundus camera comprising:

an illuminating optical system for illuminating the fundus of the eye to be inspected;

an image forming optical system having a first path of light in which the rays of light from the fundus of the eye can travel for forming an image of the fundus of the eye;

a movable reflecting member movable between a first position within said first path of light and a second position outside of said first path of light, said reflecting member forming a second path of light branching off from said first path of light when placed in said first position;

first means provided in said first path of light and behind said movable reflecting member for observing and/or photographing said image formed by said image forming optical system;

second means provided in said second path of light for observing and/or photographing said image of the fundus of the eye;

actuating means for actuating said first or second means to photograph;

control means connected with said actuating means for controlling the movement of said movable reflecting member between said first and second positions, said control means including: first control means for normally keeping said reflecting member in said second position, inserting said reflecting member into said first position as said actuating means actuates said second means, and after a definite time interval moving said reflecting member into said second position; and second control means for normally keeping said reflecting member in said first position, moving said reflecting member into said second position as said actuating means actuates said first means, and after a definite time interval moving said reflecting member into said first position; and changeover switch means for selectively actuating said first or second control means.

BRIEF DESCRIPTION OF THE DRAWINGS

The present invention will now be described, by way of example, with reference to the accompanying drawings, in which.

DESCRIPTION OF THE PREFERRED EMBODIMENTS

Figure 1:
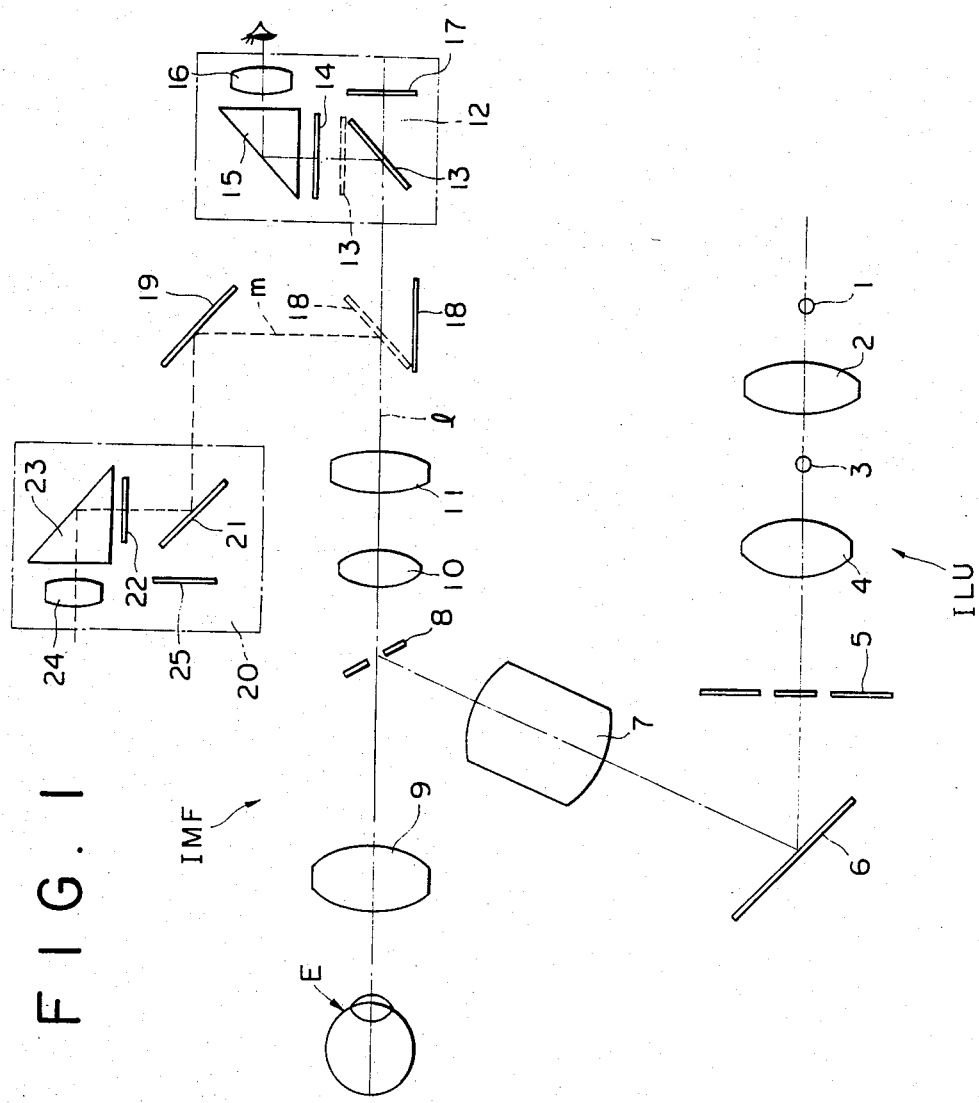
FIG. 1 is a schematic diagram showing the optical systems of an embodiment of the eye fundus camera according to the present invention.

Now referring to FIG. 1, there is schematically shown the optical systems of an embodiment of the eye fundus camera according to the present invention. The eye fundus camera includes an illuminating optical system ILU for directing light toward the fundus of the eye E to be inspected.

The illuminating optical system ILU has a first light source 1 which is adapted to emit light when observation is made. The light from the light source 1 is converged by a relay lens 2 to form an image of the light source at a point, where a second light source 3 is provided. The second light source 3 is adapted to emit light when a photograph is taken. A relay lens 4 converges the light from the light source 1 or 3. The light having passed through the relay lens 4 reaches a plate 5 having therein an annular aperture. A reflector 6 deflects the light having passed through the annular aperture of the plate 5 toward a relay lens 7. The light having passed through the lens 7 then reaches a reflector 8 having therein an opening. The reflector 8 reflects light from the relay lens 7 toward an objective lens 9, through which the light is directed toward the fundus of an eye directed at a prescribed distance toward the objective lens 9.

An image of the fundus of the eye E is formed by an optical system IMF which includes the objective 9. The light reflected from the fundus of the eye E is converged by the objective 9 to once form an image of the fundus and then diverges and passes through the opening of the reflector 8. The light is then converged by a focusing lens 10 and an image forming lens 11 to form an image of the eye fundus.

A first observing and photographing apparatus 12 receives the light from the image forming optical system IMF. The apparatus 12 for observing and photographing the eye fundus comprises means for observing, which is formed by an optical viewfinder, and means for photographing which is formed by a shutter (not shown) and a film plane 17. When observation is made, a reflector 13 is placed in front of the film plane 17, as shown in a solid line in FIG. 1, to deflect the light toward a plane 14 where the image of the eye fundus is formed. The image formed on the plane 14 can be observed through a prism 15 and an eyepiece 16. When a photograph is taken, an exposure switch (described later) is operated. Then, the reflector 13 is swung out of the path of light l and kept away from the path of light l for a predetermined time period, as shown in broken lines in FIG. 1. While the reflector 13 is kept away from the path of light, the shutter (not shown) is released to expose the film 17.

A movable reflecting member or reflector 18 is mounted between the image forming lens 11 and the first observing and photographing apparatus 12. The mirror 18 is designed to be driven by electromagnetic means (described later) to move between a first position (shown in broken lines) within the first path of light l and a second position (shown in a solid line) outside of the first path of light l. When positioned in the first position within the first path of light l, the movable mirror 18 forms a second path of light m which branches off from the first path of light l. The second path m is bended by a fixed reflector 19 and extends to a second observing and photographing apparatus 20.

The second observing and photographing apparatus 20 comprises, as the first apparatus 12 does, a reflector 21, a plane 22 where the image can be formed, a prism 23, an eyepiece 24, and a film plane 25.

Figure 2:
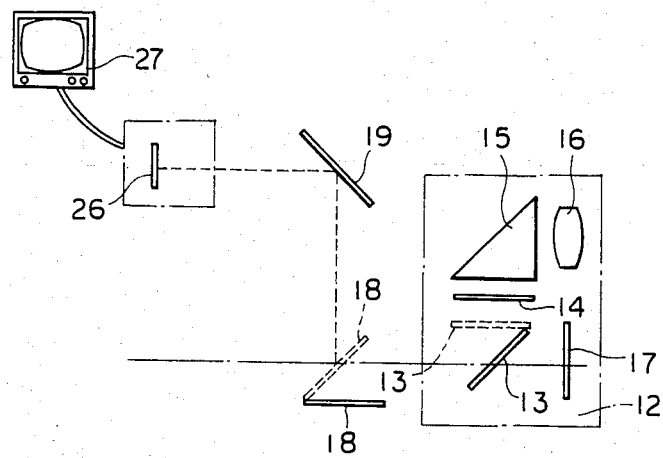
FIG. 2 is a schematic diagram showing another example of the second observing and/or photographing apparatus.

Though in the embodiment shown in FIG. 1 both the apparatus 12 and 20 have means for observation through an eyepiece 16 or 24, such means of one apparatus can be dispensed with. Further, the second apparatus 20 can be replaced by a display system for providing a visual display of the eye fundus. The display system can comprise a camera tube 26 and a television receiver 27, as shown in FIG. 2.

Figure 3:
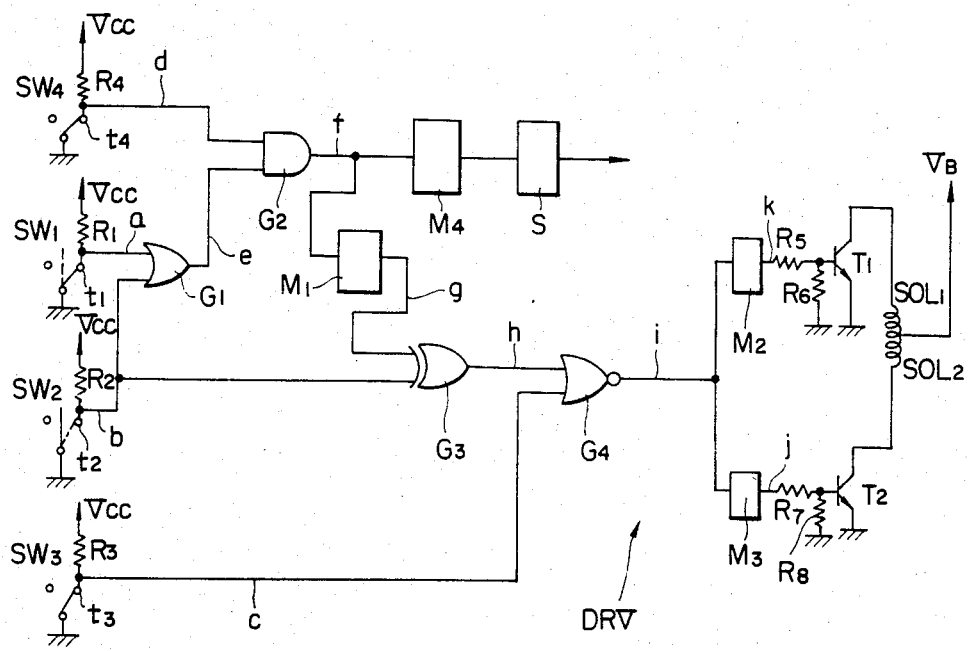
FIG. 3 is a schematic circuit diagram showing an example of the control circuit.

FIG. 3 is a schematic diagram of an example of the control circuit for controlling the operation of the eye fundus camera. In this Figure, reference SW1 denotes a first manually operated selection switch whose fixed contact t1 is connected through a resistor R1 to a constant voltage source Vcc. The contact t1 is also connected to an input of an OR gate G1 whose another input is connected to a fixed contact t2 of a second maually operated selection switch SW2. The contact t2 is also connected to a constant voltage source Vcc through a resistor R2.

The first and second selection switches SW1 and SW2 are "seesaw" switches; i.e. they are interlocked together so that closing of one switch causes opening of the other.

The output of the OR gate G1 is connected to an input of an AND gate G2 whose another input is connected to a fixed contact t4 of a manually operated, normally closed exposure switch SW4. The contact t4 is connected through a resistor R4 to a constant voltage source Vcc. The output of the AND gate G2 is connected through a monostable multivibrator M1 to an input of an exclusive OR gate G3 whose another input is connected to the fixed contact t2 of the second selection switch SW2. The output of the exclusive OR gate G3 is connected to an input of a NOR gate G4 whose another input is connected to a contact t3 of a third manually operated, normally closed selection switch SW3. The contact t3 is connected through a resistor R3 to a constant voltage source Vcc.

The output from the NOR gate G4 is supplied to a circuit DRV for driving the movable mirror 18. The mirror driving circuit includes two monostable multivibrators M2 and M3 connected to receive the output from the NOR gate G4. These multivibrators M2 and M3 are arranged to produce an output in response to the rise and fall, respectively, of the output level from the gate G4. The output from one multivibrator M2 is supplied to the base of a transistor T1 through a resistor R5, the base being connected through a resistor R6 to ground. Likewise, the output from the other multivibrator M3 is supplied to the base of another transistor T2 through a resistor R7, the base being connected through a resistor R8 to ground. The emitters of both transistors T1 and T2 are directly connected to ground, while the collectors of T1 and T2 are connected through solenoids SOL1 and SOL2, respectively, to a constant voltage source $V_B$.

The solenoids SOL1 and SOL2 form part of a "latching" solenoid magnet which is constructed such that, when one solenoid SOL1 is energized, it drives the movable mirror 18 into its first position within the first path of light l where the mirror is latched by a mechanical latch (not shown) until driven in the reversed direction. When the other solenoid SOL2 is energized, the solenoid magnet drives the mirror 18 from its first position into its second position outside the path of light l, where the mirror is latched mechanically until the first solenoid SOL1 is again energized.

As compared with a "rotary" solenoid, the latching solenoid magnet has an advantage that it can maintain the mirror 18 in position without energizing any of the solenoids SOL1 and SOL2, i.e. without evolution of Joule heat.

Meanwhile, a monostable multivibrator M4 connected to receive the output from the AND gate G2 produces an output signal for a constant time period in response to the rise of its input level. The duration of the output signal from the monostable multivibrator M4 is chosen at a value, e.g. 300 msec, within which bound of the movable mirror 18 arising from its being driven by the solenoid magnet will terminate.

An exposure control circuit S connected to receive the output from the monostable multivibrator M4 issues a series of signals in response to the termination of the output from the monostable multivibrator M4, this termination being a "start-of-photographing" signal.

In response to the signals from the exposure control circuit S, the reflector 13 or 21 of a selected one of the apparatus 12 or 20 is swung out of the path of light l or m; the light source 3 is energized to emit light; the shutter (not shown) of the selected one of the apparatus 12 or 20 is released; and after a definite time the reflector 13 or 21 is returned to its original position. Thus, one cycle of operations of exposing the film is completed.

The operation of the eye fundus camera shown in FIGS. 1 and 3 will now be described with reference to the time charts of FIGS. 4 to 6.

Figure 4:
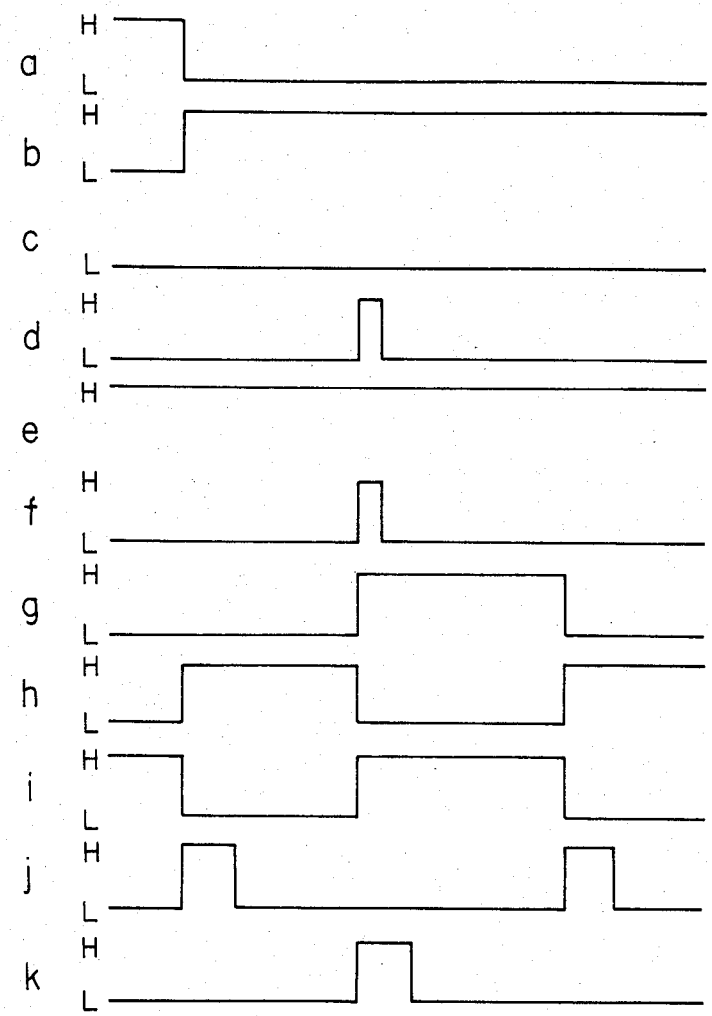
FIGS. 4, 5, and 6 are diagrams showing waveforms occurring at various points of the electric circuit of FIG. 3 during different modes of operation.

FIG. 4 shows waveforms occurring at various points of the electric circuit shown in FIG. 3 during a first mode of operation in which the first observing and photographing apparatus 12 is used for observation while the second observing and photographing apparatus 20 for photographing. When the first selection switch SW1 is closed and thus its contact t1 is connected to ground, the potential at the point a turns from high to low. At the same time, the second switch SW2 is automatically opened (as previously mentioned, these two switches SW1 and SW2 are interlocked "seesaw" switches) and thus the potential at its fixed contact t2 or the point b turns from low to high.

The third selection switch SW3 and the exposure switch SW4, both normally closed as previously mentioned, are then left closed and the potential at points c and d is maintained low. The potential at the points d and e is maintained low and high, respectively, notwithstanding the manual operation applied to the switch SW1 and the resulting potential change at the points a and b, so that the output f from the AND gate G2 is also maintained low and the potential at the output g of the monostable multivibrator M1 is maintained low.

On the other hand, when the first switch SW1 is closed, the output from the exclusive OR gate G3 turns from low to high in response to the potential change at the point b, so that the output e from the NOR gate G4 turns from high to low. The monostable multivibrator M3 is then actuated to produce an output signal which in turn makes conductive the transistor T2. The solenoid SOL2 is energized by the current through the transistor T2 so that the movable mirror 18 is swung out of the first path of light 1 as previously mentioned. Then, it is possible to observe the eye fundus through the viewfinder of the first observing and photographing apparatus 12.

When the exposure switch SW4 is opened after the observation under such conditions, the potential at the point d turns from low to high. As a result, the potential at the point f turns from low to high and the monostable multivibrator M1 is actuated and the potential at the point g turns from low to high. Then, the potential at h turns from high to low, and at i from low to high, so that the monostable multivibrator M2 responsive to the rise of its input level produces an output k. The transistor T1 is made conductive in response to the output k from the monostable multivibrator M2. The solenoid SOL1 is then energized by the current through the transistor T1, so that the movable mirror 18 is inserted into the first path of light 1. Then, the mirror 18 positioned in the first path of light 1 forms the second path of light m toward the fixed mirror 19 and then a photograph of the eye fundus is taken.

The monostable multivibrator M1 maintains its high level output g for a definite time. When the output g from the multivibrator M1 terminates, the potential at the point h turns from low to high, and thus at the point i from high to low. The monostable multivibrator M3 produces an output in response to the fall of its input level i; the transistor T2 is turned conductive; the solenoid SOL2 is energized to remove the movable mirror 18 from the first path of light 1. Then, observation through the first observing and photographing apparatus 12 is possible.

Figure 5:
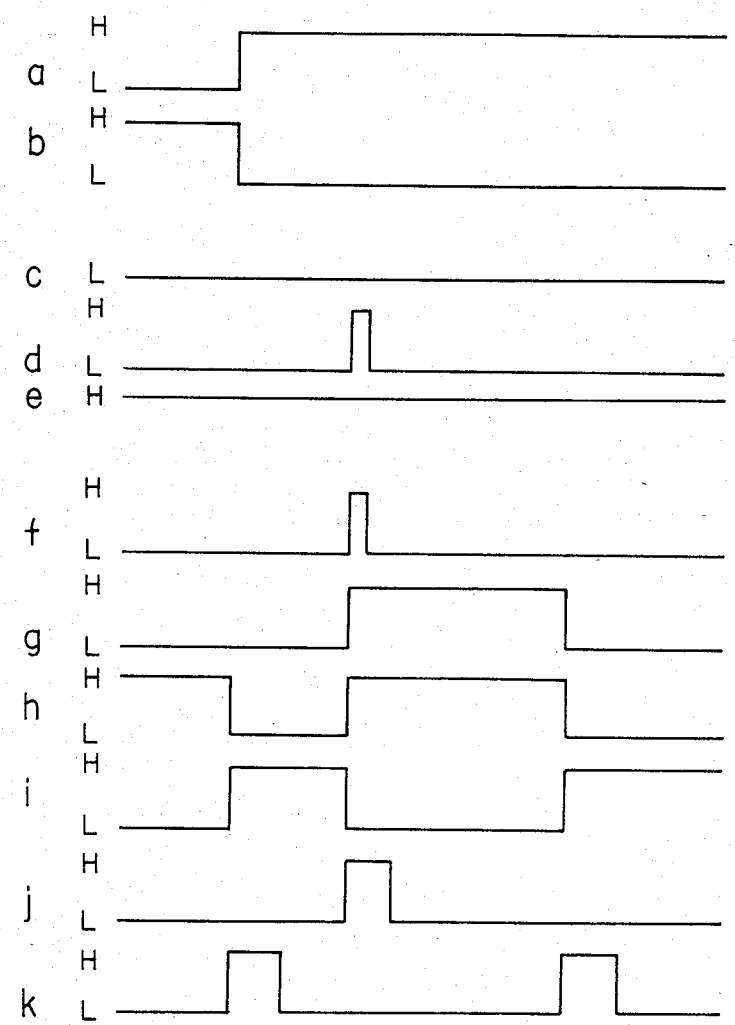

FIG. 5 shows waveforms occurring at various points of the electric circuit shown in FIG. 3 during a second mode of operation in which the first apparatus 12 is used for photographing, while the second apparatus is used for observation. The second apparatus is the observing and photographing apparatus 20 (FIG. 1) or the television receiver 27 associated with the camera tube 26 (FIG. 2).

To carry out the second mode of operation, the second selection switch SW2 is closed. Then, the movable mirror 18 is inserted into the first path of light 1, enabling observation through the second observing and photographing apparatus 20 or the television receiver 27. To take a photograph, the exposure switch SW4 is opened so that the mirror 18 is removed from the first path of lght 1. After completion of the exposure, the movable mirror 18 is returned to the first position in the first path of light 1.

Figure 6:
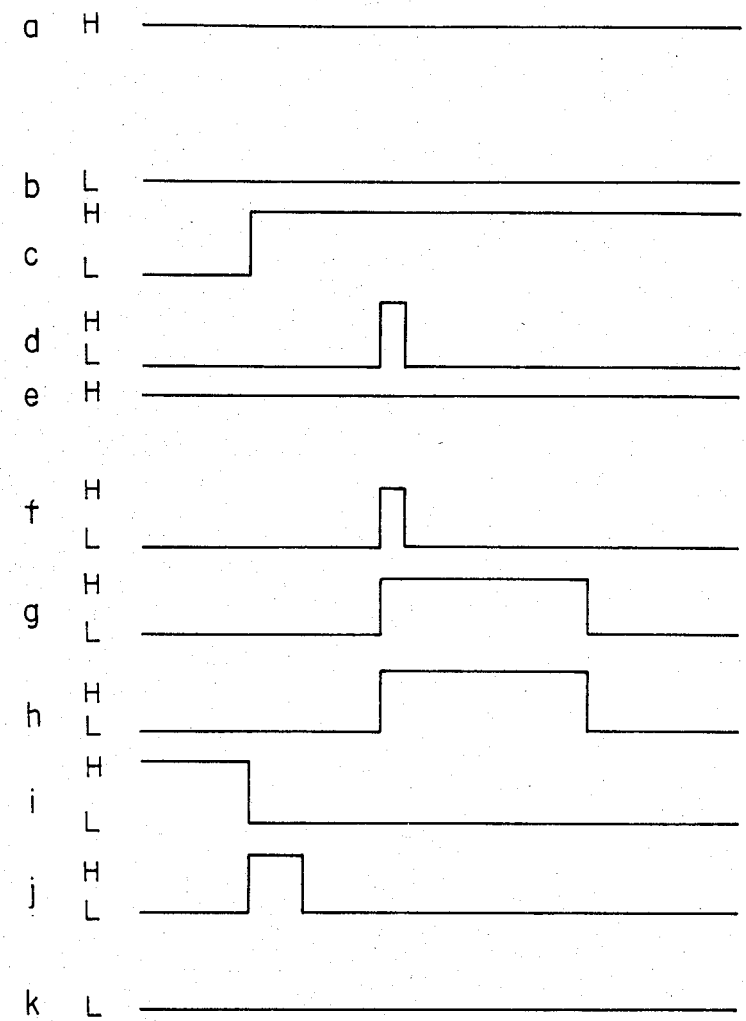

FIG. 6 shows waveforms occurring during a third mode of operation in which both observation and photographing are made by means of the first observing and photographing apparatus 12.

To carry out the third mode of operation, the third selection switch SW3, which is normally closed, is opened. Then the movable mirror 18 is removed out of the first path of light 1 and kept away from the path 1 for observation and photographing.

Detailed description of waveforms of FIGS. 5 and 6 will be similar to that of FIG. 4, and thus will not be given.

As will be understood from the above description, the eye fundus camera according to the present invention can be mounted with at least two types of observing and/or photographing apparatus by which various kinds of observation and photographing can be carried out by simple operation of a number of selection switches.

What is claimed is:
1. An eye fundus camera comprising:
an illuminating optical system for illuminating the fundus of the eye to be inspected;
an image forming optical system having a first path of light in which the rays of light from the fundus of the eye can travel for forming an image of the fundus of the eye;
a movable reflecting member movable between a first position within said first path of light and a second position outside of said first path of light, said reflecting member forming a second path of light branching off from said first path of light when placed in said first position;
first means provided in said first path of light and behind said movable reflecting member for observing and/or photographing said image formed by said image forming optical system;
second means provided in said second path of light for observing and/or photographing said image of the fundus of the eye;
actuating means for actuating said first or second means to photograph;
control means connected with said actuating means for controlling the movement of said movable relecting member between said first and second positions, said control means including: first control means for normally keeping said reflecting member in said second position, inserting said reflecting member into said first position as said actuating means actuates said second means, and after a definite time interval moving said reflecting member into said second position; and second control means for normally keeping said reflecting member in said first position, moving said reflecting member into said second position as said actuating means actuates said first means, and after a definite time interval moving said reflecting member into said first position; and changeover switch means for selectively actuating said first or second control means.

2. An eye fundus camera as claimed in claim 1, in which said control means further includes a third control means for keeping said reflecting member in said second position irrespective of the action of said actuating means.

3. An eye fundus camera as claimed in claim 1, in which said first means comprises: a film plane where the image of the eye fundus is to be formed; a first movable mirror provided in front of said film plane and normally kept in a third position within said first path of light and withdrawn from said position as said actuating means operates; and a viewfinder part provided in the path of light reflected from said movable mirror.

4. An eye fundus camera as claimed in claim 3, in which said second means comprises: a film plane where the image of the eye fundus is to be formed; a second movable mirror provided in front of said film plane and normally kept in a fourth position within said second path of light and withdrawn from said fourth position as said actuating means operates; and a second viewfinder part provided in the path of light reflected from said movable mirror.

5. An eye fundus camera as claimed in claim 3, in which said second means comprises a camera tube means for converting the image of the eye fundus into an electrical signal, and a display tube responsive to said electrical signal for providing a visual display of the eye fundus.

* * * * *